United States Patent
Corthals et al.

(10) Patent No.: US 10,519,087 B2
(45) Date of Patent: Dec. 31, 2019

(54) PROCESS FOR THE CONVERSION OF METHANE INTO PROPANAL

(71) Applicant: Dow Global Technologies LLC, Midland, MI (US)

(72) Inventors: Steven L. F. Corthals, Wachtebeke (BE); Thomas Davidian, Ghent (BE); Gerolamo Budroni, Terneuzen (NL); Peter E. Groenendijk, Hulst (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/304,469

(22) PCT Filed: Jun. 13, 2017

(86) PCT No.: PCT/US2017/037159
§ 371 (c)(1),
(2) Date: Nov. 26, 2018

(87) PCT Pub. No.: WO2018/005074
PCT Pub. Date: Jan. 4, 2018

(65) Prior Publication Data
US 2019/0292122 A1    Sep. 26, 2019

Related U.S. Application Data

(60) Provisional application No. 62/356,786, filed on Jun. 30, 2016.

(51) Int. Cl.
| | |
|---|---|
| *C07C 45/00* | (2006.01) |
| *C01B 3/00* | (2006.01) |
| *C07C 45/50* | (2006.01) |
| *C07C 2/84* | (2006.01) |
| *C01B 3/36* | (2006.01) |
| *C07C 5/333* | (2006.01) |

(52) U.S. Cl.
CPC .............. *C07C 45/505* (2013.01); *C01B 3/36* (2013.01); *C07C 2/84* (2013.01); *C07C 5/333* (2013.01); *C01B 2203/0283* (2013.01)

(58) Field of Classification Search
CPC ................................ C07C 45/505; C01B 3/36
See application file for complete search history.

(56) References Cited

U.S. PATENT DOCUMENTS

| 8,884,070 B2 | 11/2014 | Franke et al. |
| 2012/0065412 A1 | 3/2012 | Abdallah et al. |
| 2014/0171707 A1 | 6/2014 | Nyce et al. |
| 2017/0037159 A1 | 2/2017 | Hasebe et al. |

FOREIGN PATENT DOCUMENTS

| WO | 9622265 A1 | 7/1996 |
| WO | 2011059855 A1 | 5/2011 |
| WO | 2012118888 A2 | 9/2012 |
| WO | 2013098272 A1 | 7/2013 |
| WO | 2014143880 A1 | 9/2014 |
| WO | 2015047735 A1 | 4/2015 |
| WO | 2015057753 A1 | 4/2015 |
| WO | 2018005074 A1 | 1/2018 |

*Primary Examiner* — Sikarl A Witherspoon
(74) *Attorney, Agent, or Firm* — Brian L. Mutschler

(57) ABSTRACT

The present invention provides methods for making propanal in a reaction comprising the oxidative coupling of methane (OCM) and oxygen as a reactant stream in a gas phase reaction, preferably in the presence of water or steam, to form ethylene, ethane, carbon dioxide ($CO_2$), water and syngas (CO and $H_2$) in a first reactor as an ethylene stream, and then forming propanal in a second reactor by feeding to the second reactor the ethylene stream with the syngas from the first reactor in the gas phase and hydroformylating in the presence of a catalyst for a water shift reaction. In the method, the ratio of $H_2$ to CO in the syngas is maintained by either co-feeding steam into the first reactor or the second reactor to generate additional $H_2$ in the syngas, or by forming CO in the second reactor from the water shift reaction by feeding the $CO_2$ from the ethylene stream into the second reactor.

10 Claims, 2 Drawing Sheets

PROCESS FOR THE CONVERSION OF METHANE INTO PROPANAL

The present invention relates to methods for making propanal, such as for use in making methyl methacrylate (MMA), in a reaction comprising oxidative coupling of methane and oxygen (OCM reaction) in a first reactor in a gas phase reaction, preferably, in the presence of water or steam, to form a stream of ethylene, ethane, water, syngas (CO and $H_2$) and carbon dioxide, and forming propanal by hydroformylation of the ethylene with the syngas in a second reactor wherein after the OCM reaction, the molar ratio of the syngas to the total amount of ethylene and ethane after the OCM reaction ranges from 2:1 to 10:1, or, preferably, from 2.5:1 to 5:1, or, more preferably, from 3.2:1 to 4.5:1, and, further wherein the molar ratio of total $CO_2$ and CO to (ethylene+ethane) ranges from 0.97:1 to 5:1, or, preferably, from 1:1 to 4:1, or, more preferably, from 1.1:1 to 2.5:1.

The development of extraction methods for shale gas has had a large impact on the feedstock availability of natural gas. Current shale gas and more generally natural gas, developments are making it a cheap and abundant source of hydrocarbons. These feedstocks are gas mixtures containing typically 80-99% methane, 1-20% ethane, 1-5% higher hydrocarbons and other non hydrocarbon constituent such as $CO_2$ and nitrogen. However, the larger fraction "methane" today is mainly used as fuel or as feedstock for syngas, a mixture of CO and $H_2$. Thus, converting methane or shale gas directly into useful products remains today a technical challenge.

Today, one of the most explored routes for the conversion of methane into products is oxidative coupling of methane or OCM. OCM can be used to make ethylene which can be used itself or hydroformylated into propanal (propionaldehyde) with the addition of syngas catalyzed by a NiS catalyst. See S. S. C. Chuang, *Applied Catalysis,* 66 (1990) L1, also see the "example section". Propanal can be converted to methacrolein via condensation with formaldehyde. Oxidative esterification of methacrolein results in the formation of methyl methacrylate (MMA). The oxidative coupling of methane to ethylene reaction can be expressed, as follows (the arrow meaning it is an equilibrium reaction in which favorable equilibrium goes to the right side of the equation):

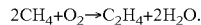

$$2CH_4 + O_2 \rightarrow C_2H_4 + 2H_2O.$$

Nevertheless, a drawback of OCM remains that the desired products (e.g. ethylene) are more reactive to oxygen than methane. As the concentrations of such products increase, so do side reactions with them. Because the OCM reaction occurs at high temperatures (700-1000° C.), the choice of a catalyst has little effect on the side reactions, which happen anyway. As a result, the majority of methane is non-selectively oxidized to carbon monoxide or carbon dioxide. In addition, conventional OCM methods require costly separation of the ethylene produced from the unconverted methane and the byproducts $CO_2$, CO, ethane, and hydrogen from OCM.

Green et al., in "High yield synthesis of propanal from methane and air", *Catalysis Letters* 13, (1992) at 341-347 discloses OCM of methane and air to make ethylene, formation of syngas from partial oxygenation of methane, and then hydroformylation of the OCM product and syngas to form propanal. However, the method separately forms syngas by partial oxidation of waste methane gas, otherwise the amount of $H_2$ and CO would be too low for hydroformylation; and hydroformylation is carried out in the liquid phase after removing each of $CO_2$ and $H_2O$ from OCM through a trap.

The conversion of methane via OCM to a mixture containing ethylene has not yet found commercial application because of the drawbacks described in the previous two paragraphs.

The present inventors have endeavored to find a simpler, process for the oxidative coupling of methane followed by hydroformylation to make propanal.

SUMMARY OF THE INVENTION

1. In accordance with the present invention, methods for making propanal in a reaction comprising the oxidative coupling of methane (OCM reaction) and oxygen as a reactant stream, preferably, the reactant stream further including water or steam, in a gas phase reaction to form ethylene, ethane, carbon dioxide ($CO_2$), water and syngas (CO and $H_2$) as an ethylene stream in a first reactor containing an OCM zone and a downstream thermal cracking zone to form ethylene from ethane, and then forming propanal in a second reactor by feeding to the second reactor the ethylene stream from the first reactor in the gas phase and hydroformylating the ethylene stream to form a propanal containing product stream in the presence of a catalyst for a water gas shift reaction in which water and carbon monoxide (CO) form from carbon dioxide and hydrogen gas ($H_2$) and for the hydroformylating, wherein the molar ratio of the syngas to the total amount of ethylene and ethane in the ethylene stream before the downstream thermal cracking zone ranges from 2:1 to 10:1, or, preferably, from 2.5:1 to 5:1, or, more preferably, from 3.2:1 to 4.5:1, and, further wherein the molar ratio of total $CO_2$ and CO to total ethylene and ethane in the ethylene stream before the downstream thermal cracking zone ranges from 0.97:1 to 5:1, or, preferably, from 1:1 to 4:1, or, more preferably, from 1.1:1 to 2.5:1.

2. In the methods in accordance with the present invention as set forth in item 1, further comprising adjusting the molar ratio of $H_2$ to CO in the syngas in the ethylene stream by co-feeding steam into the second reactor and/or into the first reactor, preferably, the first reactor, to generate additional $H_2$ in the syngas in any case wherein the molar ratio of the $H_2$ to CO in the syngas in the ethylene stream leaving the downstream thermal cracking zone of the first reactor is below 1:1 or, alternatively, by reacting the $CO_2$ and $H_2$ from the ethylene stream of the first reactor in the second reactor to generate additional CO in the syngas in the presence of a catalyst for a water gas shift reaction.

3. In the methods in accordance with the present invention as set forth in item 2, above, wherein the steam is generated by compressing the ethylene stream output from the first reactor to form a compressed OCM fluid stream containing water, removing water from the compressed OCM fluid stream and reheating the water to form steam.

4. In the methods in accordance with the present invention as set forth in item 3, above, wherein the reheating of the water to form steam comprises using the water in a heat exchanger to compress the output from the first reactor and heat the water.

5. In the methods in accordance with the present invention as set forth in any one of items 2, 3, or 4, above, wherein the catalyst for a water gas shift and for the hydroformylating is a sulfide catalyst, such as a metal sulfide catalyst, for example, CoMoSK or, preferably, NiS, or a double layer catalyst wherein each layer contains a sulfide and the first layer acts as water gas shift catalyst while the second layer acts as hydroformylation catalyst.

6. In the methods in accordance with the present invention as set forth in any one of items 1, 2, 3, 4, or 5, wherein the first reactor comprises an OCM zone and a downstream thermal cracking zone in which ethylene formation comprises dehydrogenating any ethane in the OCM zone to form ethylene in the downstream thermal cracking zone using the heat from the first reactor to drive the dehydrogenating reaction.

7. In the methods in accordance with the present invention as set forth in any of items 1 to 6, above, wherein the temperature in the first reactor or the OCM zone thereof ranges from 700 to 1000° C., or preferably, from 750 to 1000° C., and wherein the pressure in the first reactor or the OCM zone thereof ranges from 100 to 1000 kPa, or, preferably, from 100 to 500 kPa.

8. In the methods in accordance with the present invention as set forth in any of items 1 to 7, above, wherein after hydroformylating the ethylene stream, the propanal containing product stream comprising propanal, methane, ethane, propanol, carbon dioxide, water vapor and syngas is fed to a separator, such as a gas-liquid separator, gas-gas separator, or a distillation column.

9. In the methods in accordance with the present invention as set forth in item 8, above, wherein the methane is recycled to the first reactor and ethane is recycled to a downstream thermal cracking zone in the first reactor.

10. In the methods in accordance with the present invention as set forth in any one of items 1 to 9, above, wherein the forming propanal in the second reactor comprises hydroformylating the ethylene with the syngas from the ethylene stream at a temperature of from 250 to 400° C., or, preferably, from 280 to 340° C. and at a pressure of from 100 to 10,000 kPa or, preferably, from 5,000 to 10,000 kPa.

11. In the methods in accordance with the present invention as set forth in any one of items 1 to 10, above, wherein the initial molar ratio of methane to oxygen in the first reactor for the oxidative coupling of methane ranges from 2.25:1 to 5.5:1 or, preferably, from 2.5:1 to 4.75:1.

12. In the methods in accordance with the present invention as set forth in any of items 1 to 11, above, wherein the first reactor, the second reactor and all streams leading directly or indirectly from the first reactor to the second reactor are in an enclosed or sealed system.

13. In the methods in accordance with the present invention as set forth in any of items 1 to 12, above, wherein the first reactor is an adiabatic reactor or an isothermal reactor, such as a multitubular reactor.

14. In the methods in accordance with the present invention as set forth in any of items 1 to 13, above, wherein the second reactor is an adiabatic reactor or an isothermal reactor, such as a multitubular reactor.

Figure 1:
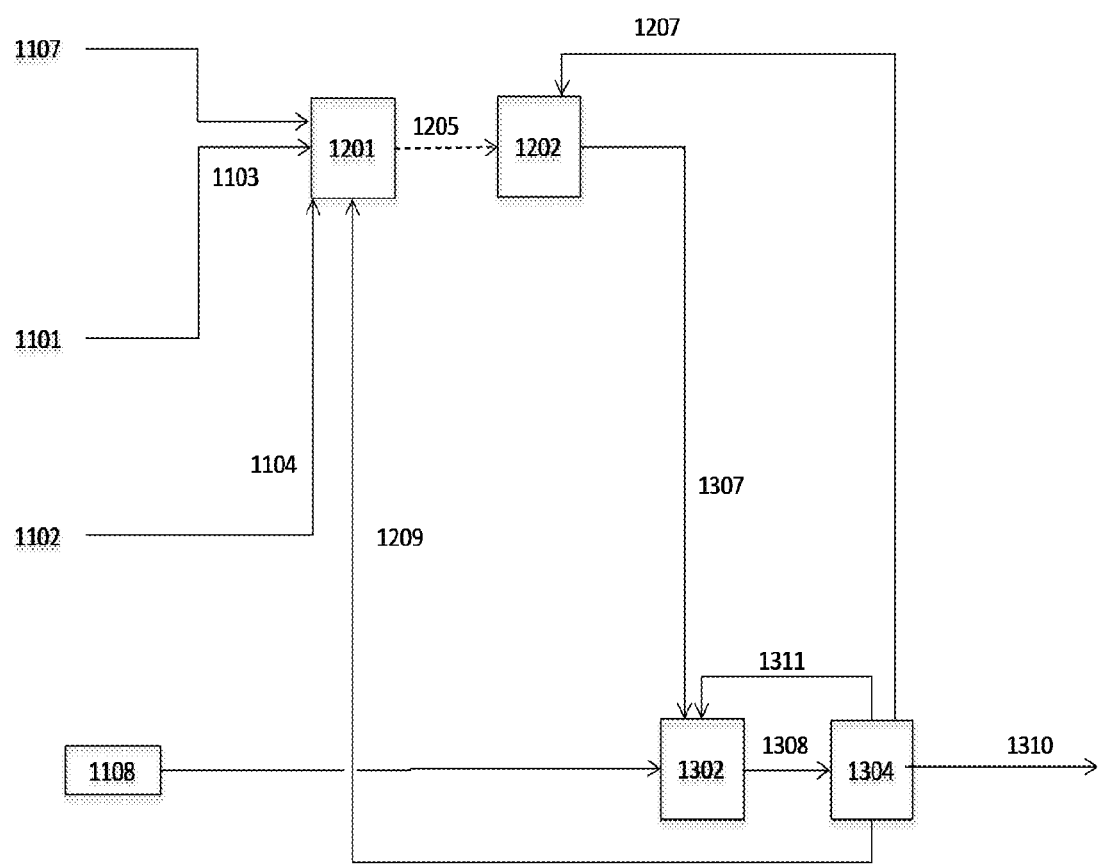
FIG. 1 is a schematic of the methods of the present invention.

All temperatures are in ° C., unless otherwise indicated.

Unless otherwise indicated, all temperatures are room temperature (22-23° C.) and all pressures are standard pressure (~760 mm/Hg).

Unless otherwise indicated, any term containing parentheses refers, alternatively, to the whole term as if no parentheses were present and the term without them, and combinations of each alternative. Thus, the term "(m)ethane" refers to methane, ethane, or mixtures thereof.

All ranges are inclusive and combinable. For example, the term "a range of 50 to 3000 cPs, or 100 or more cPs" would include each of 50 to 100 cPs, 50 to 3000 cPs and 100 to 3000 cPs.

As used herein, the term "ASTM" refers to the publications of ASTM International, West Conshohocken, Pa.

A "stage" in a distillation column is a tray in the case of a tray tower or an equilibrium stage in the case of a packed tower.

As used herein, the abbreviation "wt. %" stands for weight percent.

The present invention presents much simplified oxidative coupling of methane (OCM) and hydroformylation methods for making propanal, such as for use in making methyl methacrylate. The present invention solves a problem with the production of an ethylene/syngas mixture via conventional OCM wherein a low $H_2/CO$ molar ratio of the syngas creates a hydrogen deficiency for the hydroformylation reaction. A low $H_2/CO$ ratio limits the hydroformylation reaction to the hydrogen available, leading to unconverted ethylene. The present invention also solves a problem wherein an excessive $H_2/CO$ molar ratio limits the hydroformylation reaction to the CO available, leading to ethane and propanol in the product stream. In both cases, a low ethylene conversion to propanal leads to lower process efficiency and the need to add costly equipment to the process such as separation equipment, a recycling capability, and/or increased reactor size. To overcome this problem, the present inventors discovered that co-feeding a controlled amount of steam or carbon dioxide to a hydroformylation catalyst which has water gas shift ability under the process conditions will enable adjustment of the molar ratio of $H_2$ to CO in the syngas to the desired $H_2/CO$ molar ratio entering a hydroformylation reactor, which is 0.2:1 to 9:1, or 0.4:1 or higher or, preferably, from 0.8:1 to 6.0:1. Accordingly, the methods of the present invention do not convert the syngas produced during OCM back to methane; rather, the methods of the present invention use the syngas produced during OCM to react with the ethylene in a gas phase hydroformylation reaction. The syngas produced during OCM in accordance with the present invention eliminates the need to produce syngas in a separate reforming process using a reformer reactor and avoids the necessity of adding syngas to an OCM output stream to replenish $H_2$ or CO. Further, the present invention avoids the necessity of any cryogenic or other separation of ethylene from an OCM reaction. Further, the present invention avoids the need to make additional syngas for hydroformylation in a separate reformer reactor.

In accordance with the present invention additional hydrogen for syngas may be generated by co-feeding steam into a hydroformylation reaction using the water-gas shift reaction:

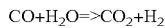

Because the water gas shift reaction is an equilibrium reaction, its direction can be reversed when there is a large or excessive amount of hydrogen gas. Accordingly, a reverse water gas shift ($CO_2 + H_2 \rightarrow CO$ and $H_2O$) performed in the hydroformylation reaction can be used to generate more CO for syngas as needed to adjust the ratio of $H_2$ to CO in the syngas.

In accordance with the present invention, preferably, the reactant stream in the OCM reaction comprises water or, as the temperature of the OCM reaction is well above the boiling point of water, steam. Even without added water or steam, the OCM reaction generate some water in the ethylene stream; however, added water or steam facilitates the water gas shift reaction. In whatever form it takes, water or steam in the reactant stream of the OCM reactor participates in the water shift reaction in the second reactor, thereby enabling the adjustment of ratio of $H_2$ to CO in the syngas which is reacted in the second reactor.

In accordance with the methods of the present invention, the generation of either or both of CO or $H_2$ will result in additional syngas for the hydroformylation reaction. Such generation of additional syngas can be used insure that the molar ratio of the syngas to the total amount of ethylene and ethane in the ethylene stream ranges from 2:1 to 10:1, or, preferably, from 2.5:1 to 5:1, or, more preferably, from 3.2:1 to 4.5:1, and, further wherein the molar ratio of total $CO_2$ and CO to total ethylene and ethane in the ethylene stream ranges from 1:1 to 5:1, or, preferably, from 1.1:1 to 4:1, or, more preferably, from 1.15:1 to 2.5:1.

In accordance with the present invention, hydroformylation is a heterogeneous catalytic gas phase process that uses a catalyst, such as a metal sulfide, with a selectivity to propanal that is below the selectivity of a homogeneous catalyst for the making of propanal, such as, for example, a NiS catalyst having 70% selectivity to propanal; the main side reaction is hydrogenation of ethylene to ethane; so the result is 30% selectivity to ethane. The ethane can be recycled from a second reactor or hydroformylation reactor to the OCM reactor or first reactor which can convert the ethane to ethylene in a downstream cracking zone. The use of the less selective hydroformylation catalyst in accordance with the present invention has no negative impact on propanal yield. In addition, the metal sulfide catalyst can be used to adjust the molar ratio of $H_2$ to CO in the syngas ratio of components in the syngas because it can catalyze a water gas shift reaction.

In accordance with the present invention, a reactive separation of ethylene from an OCM product stream via hydroformylation produces propanal for the preparation of MMA. Propanal can be separated more easily from a process stream than ethylene.

In accordance with the present invention, ethane, methane and propanol are separated from the hydroformylation product stream leaving the second reactor.

In accordance with the present invention, co-feeding a desired amount of steam to a second reactor or hydroformylation reactor comprises compressing an OCM product stream into the second reactor, removing water from the compressed product stream and re-adding it as steam to the hydroformylation reactor.

In the second reactor in accordance with the present invention, the $H_2$/CO molar ratio in the syngas ranges from 0.2:1 to 9:1, or, 0.4:1 or higher, or, preferably, 0.8:1 to 6:1. The $H_2$/CO molar ration can be advantageously adjusted to enable a higher conversion of ethylene to propanal rather than to propanol.

A suitable catalyst for the water gas shift reaction and for the hydroformylation reaction is a sulfide catalyst, such as CoMoSK or NiS.

CoMoSK comprises a water gas shift reaction catalyst containing cobalt and molybdenum present in a sulfide form.

Another suitable catalyst for use in accordance with the present invention is comprises a double layer catalyst comprising the sulfide catalyst wherein the first layer acts as water gas shift catalyst and the second layer as hydroformylation catalyst.

In accordance with the present invention, the catalyst for the water gas shift reaction may be included either in a bulk form or dispersed on an oxide support such as gamma alumina.

In accordance with the present invention, to avoid re-oxidation of any catalyst due to the added steam, the hydroformylation reaction comprises continuously adding a small amount of $H_2S$ in the ethylene feed stream, such as from 0.1 and 1 vol. %, based on the total volume of the ethylene feed stream into the second reactor.

In the OCM reaction in accordance with the present invention, a methane to oxygen optimum feed ratio is at a molar ratio of from 2.25:1 to below 5.0:1 or, preferably, from 2.5:1 to 4.75:1; however, at a ratio of 5.0:1 or above, the reaction in the second reactor does not have enough syngas to effect hydroformylation.

Figure 2:
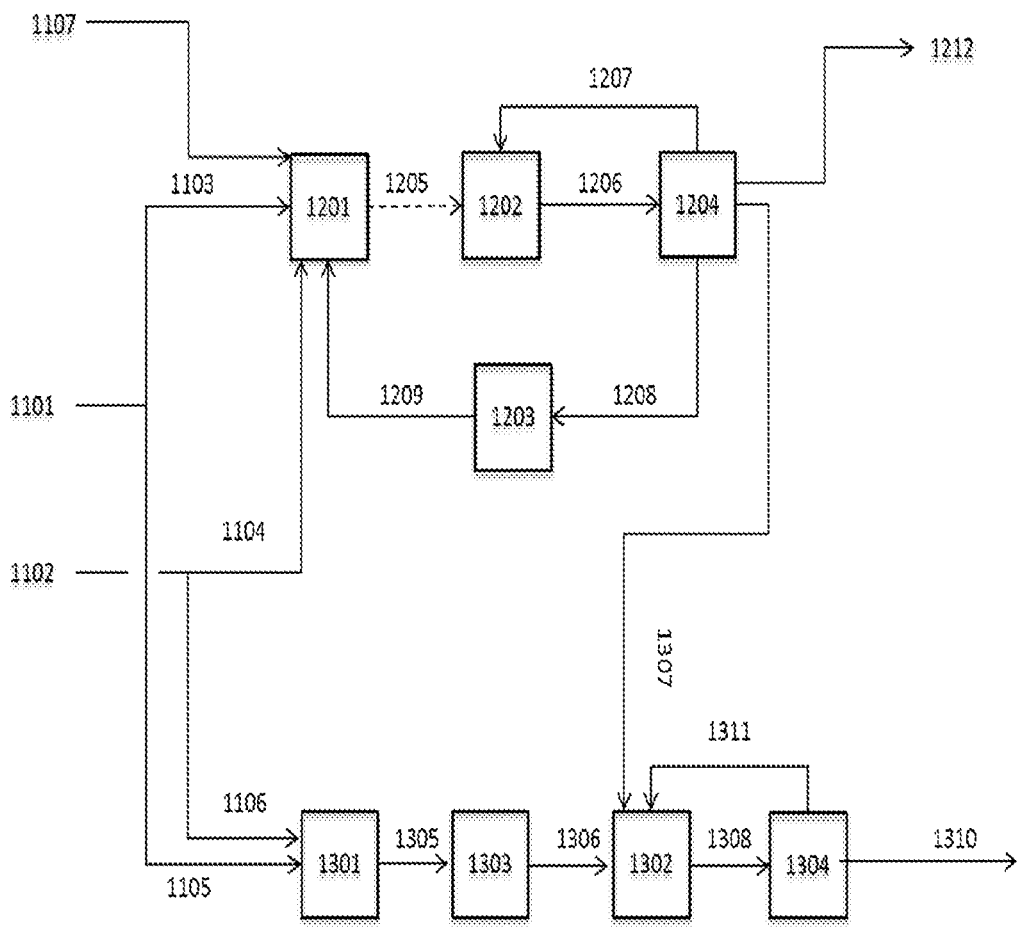
FIG. 2 is a schematic of a known process in accordance with the art.

Integrated in an enclosed system into the conventional OCM and hydroformylation reaction in FIG. 2, methane from supply (1101) and oxygen gas from supply (1102) are fed, respectively, via feed streams (1105, methane) and (1106, oxygen) methods to reforming reactor (1301) including outlet stream (1305) to make syngas. The syngas was routed through a syngas adjustment unit (1303) where needed to increase the ratio of syngas in the hydroformylation reactor (1302); the outlet stream (1305) was routed through a syngas feed stream (1306) to the hydroformylation reactor (1302). The outlet stream (1308) of the hydroformylation reactor (1302) is then fed to separation unit (1304), from which a syngas recycle stream (1311) flows back to hydroformylation reactor (1302) and from which the propanal product stream (1310) is removed.

As shown in FIG. 2, in accordance with the methods known in the art, each of $H_2O$ via supply (1107), methane or $CH_4$ from supply (1101) and oxygen gas from supply (1102) are fed, respectively, via feed streams (1103, methane) and (1104, oxygen) into (OCM) reactor (1201) and through an OCM stream (1205) into a post OCM thermal cracking zone (1202) in the OCM reactor (1201), and then through a post cracking outlet stream (1206) into a separation unit (1204). The separation unit (1204) removes ethylene from a $CO_2$ product stream (1212) a volatiles recycle stream (1208) containing $H_2$, CO, $CH_4$, and an ethane stream (1207) which is recycled to thermal cracking zone (1202) of OCM reactor (1201). The volatiles recycle stream (1207) is recycled through methanator (1203) and the resulting methane recycle stream (1209) is fed back into the OCM reactor (1201). Finally, the ethylene reaction product of the OCM reaction is fed via feed stream (1307) to a hydroformylation reactor (1302).

As shown in FIG. 1, in accordance with the methods of the present invention, each of $H_2O$ via supply (1107, not shown), methane or $CH_4$ from supply (1101) and oxygen gas from supply (1102) are fed, respectively, via gas feed streams (1103, methane) and (1104, oxygen) into an OCM reactor (1201) and via OCM stream (1205) into a post OCM thermal cracking zone (1202) in the OCM reactor (1201). Then the ethylene reaction product of the OCM reaction is fed directly via feed stream (1307) to a hydroformylation reactor (1302); and from there an outlet stream (1308) of the hydroformylation reactor (1302) is then fed to separation unit (1304), from which a syngas recycle stream (1311) flows back to hydroformylation reactor (1302) and from which the propanal product stream (1310) and a $CO_2$ product stream (1212) are removed. A methane stream (1209) is recycled to OCM reactor (1201). Finally, an ethane stream (1207) is recycled to thermal cracking zone (1202) of OCM reactor (1201). If necessary to maintain a desired ratio of $H_2$ to CO, the $CO_2$ product stream (1212) can be recycled (not shown) to hydroformylation reactor (1302). Not shown in FIG. 1, water can be condensed from ethylene feed stream (1307) and reheated to form steam for co-feeding into OCM reactor (1201) and/or hydroformylation reactor (1302).

As can be seen from comparing the invention in FIG. 1 with the conventional methods of FIG. 2, separation unit (1204) is not used at all; so, there is no need to separate ethylene from other intermediates or volatiles during the methods of making propanal. In addition, no methane is recycled to the OCM reactor (1201) prior to hydroformylation; thus, there is no reforming reactor.

The present invention provides a more efficient way to make propanal from methane, oxygen and syngas, saving the energy needed for a reforming reactor as well as that needed to remove ethylene from an OCM product stream so that one can also remove other components from that product stream to generate syngas and methane.

EXAMPLES

Abbreviations used in the Examples, below, include:
$O_2$: Oxygen Gas; $CH_4$: Methane gas; $C_3$=O: Propanal.

In the Examples below, rigorous mass balance calculations for the processes shown in FIGS. 1 and 2 were performed based on a fixed methane feed flow and fixed $CH_4$:$O_2$ feed molar ratios. For the conversion of methane into product in the OCM reaction, we assume the performance of the reaction matches the data reported in Haitao Liu et al., *Journal of Natural Gas Chemistry* Vol. 17, No. 1 (2008), pp. 59-64, (Liu et al.). Accordingly, we assumed the polynomial interpolation of the curves in FIG. 2. of Liu et al. Atom balance was used to account for the amount of water and hydrogen produced by the OCM reaction, assuming 100% mass conservation and the conversion and selectivity data in FIG. 2 of Liu et al. The conversion of the ethane in the downstream thermal cracking zone in the first reactor was assumed to have a selectivity of 77.5% to ethylene and 20% to methane, based on ultimate yields of a typical ethane cracking furnace simulated using Spyro™ suite-7 software (Technip Benelux, B. V., Pyrotec Division, Zoetermeer, N L). For the reforming reactor a syngas yield of 80% was assumed, with 20% of the methane feed being fed to the reforming reactor and used to heat the feed to the reforming reactor. For the hydroformylation process in Comparative Example 1, a homogeneous catalyst was assumed to give a selectivity of 98%, while for the heterogenous gas-phase process (Example 1) the selectivity to ethylene was assumed to be 70%, with 30% selectivity towards ethane. To account for the amount of ethane recycled in the Example 1 method, we first calculated the ethane product flow in hydroformylation in the absence of recycling. Then, the ethane recycle flow was assumed to be 30% higher because of the non-selective conversion of ethylene by the heterogeneous catalyst.

Based on equal methane and oxygen feed into the OCM or first reactor and the same energy (heat) inputs at the same pressure, the results of both a simulation of the method of the present invention with a steam co-feed into the hydroformylation reactor (Example 1) and of a simulation without the steam co-feed are shown in Table 1, below:

TABLE 1

| | | | | | | | | | |
|---|---|---|---|---|---|---|---|---|---|
| Process Inputs and Various Yields and Unit (Yield) Ratios | | | | | | | | | |
| $CH_4$:$O_2$/ ($H_2$:$CO^1$) (molar ratio) | ($H_2$ + CO):($C_2H_4$ + $C_2H_6$) (molar ratio) | (CO + $CO_2$):($C_2H_4$ + $C_2H_6$) (molar ratio) | Net $CH_4$ used (kmol/hr) | Net $O_2$ used (kmol/ hr) | $C_3$=O Carbon yield (mol %) | $CH_4$ reformer feed flow (kmol/hr) | $C_3$=O yield (kmol/hr) | $CH_4$:$C_3$=O Unit ratio (wt./wt.) | $O_2$:$C_3$=O Unit ratio (wt./wt.) |
| Stream no. | 1205 | 1205 | 1101 | 1102 | | 1105 | 1310 | | |
| Comparative Example 1 | | | | | | | | | |
| 3.0/(3.6) | 4.74 | 2.53 | 40.52 | 38.4 | 58 | 10.05 | 7.88 | 1.42 | 2.69 |
| 4.0/(5.2) | 3.81 | 1.49 | 44.04 | 31.3 | 67 | 12.48 | 9.78 | 1.24 | 1.76 |
| 4.5/(6.0) | 3.46 | 1.17 | 45.11 | 28.9 | 69 | 14.29 | 10.43 | 1.19 | 1.53 |
| 5.0/(6.9) | 3.21 | 0.97 | 45.62 | 26.9 | 71 | 13.82 | 10.84 | 1.16 | 1.37 |
| 6.0/(9.5) | 3.11 | 0.80 | 42.37 | 23.2 | 72 | 12.89 | 10.11 | 1.16 | 1.26 |
| Example 1 | | | | | | | | | |
| 3.0/(3.6) | 4.74 | 2.53 | 39.08 | 33.3 | 56 | 0.00 | 7.33 | 1.47 | 2.51 |
| 4.0/(5.2) | 3.81 | 1.49 | 38.02 | 25.0 | 72 | 0.00 | 9.10 | 1.15 | 1.52 |
| 4.5/(6.0) | 3.46 | 1.17 | 38.52 | 22.8 | 77 | 1.09 | 9.88 | 1.08 | 1.27 |
| 5.0/(6.9) | 3.21 | 0.97 | 40.30 | 21.9 | 75 | 3.73 | 10.08 | 1.10 | 1.20 |
| 6.0/(9.5)* | 3.11 | 0.80 | 38.35 | 19.5 | 74 | 5.58 | 9.40 | 1.13 | 1.14 |

[1]H2/CO ratio in OCM (ethylene) stream in 1205 before cracking zone;
*Comparative, outside the scope of the claimed invention as reformer reaction becomes significant.

OCM reaction conditions in Liu et al. at page 60 (vertical stainless steel tube reactor having a length 450 mm, and an inner diameter 100 mm, narrowed to 40 mm after the reactor, and containing a 200 ml catalyst bed of a W—Mn/$SiO_2$ catalyst run at a bed temperature of 740° C.; reaction temp rises to 800° C.; methane gas hourly space velocity (GHSV, defined as volume of gas at standard temperature and pressure/volume of catalyst/hr) is 2700 hr$^{-1}$; steam flow: 9 ml/min.) and assume that the conversion and selectivity data shown in FIG. 2 of Liu et al. all apply, except that the performance for $CH_4$:$O_2$ ratio 4.5:1 was estimated using As is shown in Table 1, above, the propanal yield of the process of the present invention in Example 1 is equal to or greater than the propanal yield in Comparative Example 1. However, at a (CO+$CO_2$) to (ethane plus ethylene) ratio within the scope of the present invention, no methane needs to be reformed after OCM and before hydroformylation, except that at a molar ratio of 1.17:1 a very small amount of methane needs to be reformed. In contrast, in all of the Comparative Examples, a substantial flow of methane needs to be reformed. Further, in contrast to Comparative Example 1, to get the same yield of propanal in Example 1, the net amount of methane used is reduced by as much as 15% (at a $CH_4:O_2$ molar ratio of 4.0:1); still further, the ratio of oxygen gas used to generate a given amount of propanal in Example 1 is reduced by as much as 15% (at a $CH_4:O_2$ molar ratio of 4.0:1).

As shown in Table 1, above, in the Example 1, the molar ratio of $H_2$ to CO in each simulation remains above 1:1; whereas in the Comparative Example 1, the molar ratio of $H_2$ to CO in each simulation remains above 1:1 only because methane is reformed.

We claim:

1. A method for making propanal in a reaction comprising the oxidative coupling of methane (OCM reaction) and oxygen as a reactant stream in a gas phase reaction to form ethylene, ethane, carbon dioxide ($CO_2$), water and syngas (CO and $H_2$) as an ethylene stream in a first reactor containing an OCM zone and a downstream thermal cracking zone to form ethylene from ethane, and then forming propanal in a second reactor by feeding to the second reactor the ethylene stream from the first reactor in the gas phase and hydroformylating the ethylene stream to form a propanal containing product stream in the presence of a catalyst for a water gas shift reaction in which water and carbon monoxide (CO) form carbon dioxide and hydrogen gas ($H_2$) and for the hydroformylating, wherein the molar ratio of the syngas to the total amount of ethylene and ethane in the ethylene stream before the downstream thermal cracking zone ranges from 2:1 to 10:1, and, further wherein, the molar ratio of total $CO_2$ and CO to total ethylene and ethane in the ethylene stream before the downstream thermal cracking zone ranges from 0.97:1 to 5:1.

2. The method as claimed in claim 1, further comprising adjusting the molar ratio of $H_2$ to CO in the syngas in the ethylene stream by co-feeding steam into the second reactor and/or into the first reactor to generate additional $H_2$ in the syngas in any case wherein the molar ratio of the $H_2$ to CO in the syngas in the ethylene stream leaving the downstream thermal cracking zone of the first reactor is below 1:1 or, alternatively, by reacting the $CO_2$ and $H_2$ from the ethylene stream of the first reactor in the second reactor to generate additional CO in the syngas in the presence of a catalyst for a water gas shift reaction.

3. The method as claimed in claim 2, wherein the steam is generated by compressing the ethylene stream output from the first reactor, to form a compressed OCM fluid stream containing water, removing water from the compressed OCM fluid stream and reheating the water therein to form steam.

4. The method as claimed in claim 3, wherein the reheating the water to form steam comprises using the water as a heat exchanger to compress the output from the first reactor.

5. The method as claimed in claim 1, wherein the catalyst for a water gas shift and for the hydroformylating is a sulfide catalyst.

6. The method as claimed in claim 1, wherein the first reactor comprises an upstream zone and a downstream thermal cracking zone in which ethylene formation comprises dehydrogenating any ethane formed in the upstream zone to form ethylene in the downstream thermal cracking zone using the heat from the first reactor to drive the dehydrogenating.

7. The method as claimed in claim 1, wherein after the hydroformylating, the propanal containing product stream, including propanal, methane, ethane, propanol, carbon dioxide, water vapor and syngas are fed to a separator.

8. The method as claimed in claim 7, wherein the methane is recycled to the first reactor and ethane is recycled to a downstream thermal cracking zone in the first reactor.

9. The method as claimed in claim 1, further comprising continuously adding $H_2S$ in the ethylene feed stream into the second reactor, in the amount of from 0.1 and 1 vol. %, based on the total volume of the ethylene feed stream.

10. The method as claimed in claim 1, wherein the first reactor, the second reactor and all streams leading directly or indirectly from the first reactor to the second reactor are in an enclosed or sealed system.

\* \* \* \* \*